(12) United States Patent
Nchekwube et al.

(10) Patent No.: US 7,229,979 B2
(45) Date of Patent: *Jun. 12, 2007

(54) HYPOESTOXIDES, DERIVATIVES AND AGONISTS THEREOF FOR USE AS STENT-COATING AGENTS

(75) Inventors: Emeka J. Nchekwube, Morgan Hill, CA (US); Emmanuel A. Ojo-Amaize, Glendora, CA (US); Howard B. Cottam, Escondido, CA (US)

(73) Assignee: Immune Modulation, Inc., Bloomington, CA (US)

( * ) Notice: Subject to any disclaimer, the term of this patent is extended or adjusted under 35 U.S.C. 154(b) by 391 days.

This patent is subject to a terminal disclaimer.

(21) Appl. No.: 10/874,384

(22) Filed: Jun. 23, 2004

(65) Prior Publication Data

US 2004/0258728 A1    Dec. 23, 2004

Related U.S. Application Data

(60) Provisional application No. 60/480,316, filed on Jun. 23, 2003.

(51) Int. Cl.
*A61K 31/665* (2006.01)
*A61K 31/535* (2006.01)
*A61K 31/335* (2006.01)

(52) U.S. Cl. .................... 514/100; 514/232.8; 514/475

(58) Field of Classification Search ............. 514/100, 514/232.8, 475, 512, 544
See application file for complete search history.

(56) References Cited

U.S. PATENT DOCUMENTS

| | | | |
|---|---|---|---|
| 5,747,474 A * | 5/1998 | Ojo-Amaize et al. | 514/46 |
| 5,801,193 A * | 9/1998 | Ojo-Amaize et al. | 514/475 |
| 5,994,328 A * | 11/1999 | Ojo-Amaize et al. | 514/100 |
| 6,001,871 A * | 12/1999 | Ojo-Amaize et al. | 514/475 |
| 6,242,484 B1 * | 6/2001 | Ojo-Amaize et al. | 514/475 |
| 6,441,025 B2 * | 8/2002 | Li et al. | 514/449 |
| 6,592,895 B2 | 7/2003 | Lang et al. | |
| 6,939,376 B2 * | 9/2005 | Shulze et al. | 623/1.42 |
| 2003/0065345 A1 | 4/2003 | Weadock | |
| 2003/0109434 A1 * | 6/2003 | Algate et al. | 514/12 |
| 2003/0229393 A1 | 12/2003 | Kutryk | |
| 2005/0112071 A1 * | 5/2005 | Ojo-Amaize et al. | 424/59 |

FOREIGN PATENT DOCUMENTS

| | | |
|---|---|---|
| EP | 1 421 909 A | 5/2004 |
| WO | 03/011212 A2 | 2/2003 |
| WO | WO 03/022266 | 3/2003 |
| WO | WO 03/065881 A | 8/2003 |

OTHER PUBLICATIONS

"Hypoestoxide, a Natural Nonmutagenic Diterpenoid with Antiangiogenic and Antitumor Activity: Possible Mechanism of Action", Ojo-Amaize et al., Cancer Research 62, pp. 4007-7014, Jul. 15, 2002.*
("The Cardiac Disease Epidemic", Doug Orr, www.medicalimagingmag.com, 2003.*
Drug-Eluting Intra-Coronary Stents: Have We Got the Magic Bullet?, Journal of Postgraduate Medicine, Jul. 1, 2003, Dhindsa, S.*
"2000 Heart and Stroke Statistical Update," American Heart Association, 1999, pp. 1-29.
Hong, Mun K. et al., "Paclitaxel-coated Gianturco-Roubin II (GR II) stents reduce neointimal hyperplasia in a porcine coronary in-stent restenosis model," Lippincott Williams & Wilkins, 2001, pp. 513-515.
Clowes, Alerander et al., "Suppression by Heparin of Smooth Muscle Cell Proliferation in Injured Arteries," Nature, vol. 265, 1977, pp. 625-626.
"Supplement to Circulation, Abstracts from the 62nd Scientific Sessions," American Heart Association, Supplement II, Circulation, vol. 80, No. 4, 1989.
Sollott, Steven J. et al., "Taxol Inhibits Neointimal Smooth Muscle Cell Accumulation After Angioplasty in the Rat," The Journal of Clinical Investigation, Inc., vol. 95, 1995, pp. 1869-1876.
Jonasson, Lena et al., "Cyclosporin A Inhibits Smooth Muscle Proliferation in the Vascular Response to injury," Proc. Natl. Acad. Sci. USA, vol. 85, 1988, pp. 2303-2306.
Marx, Steven O. et al., "Rapamycin-FKBP Inhibits Cell Cycle Regulators of Proliferation in Vascular Smooth Muscle Cells," American Heart Association, Inc., 1995, pp. 412-417.
Ojo-Amaize, Emmanuel et al., "Hypoextoxide, a Novel Anti-Inflammatory Natural Diterpene, Inhibits the Activity of $I_kB$ Kinase," Cellular Immunology 209, Academic Press, 2001, pp. 149-157.
Ojo-Amaize, Emmanuel et al., "Hypoestoxide, a Natural Nonmutagenic Diterpenoid with Antiangiogenic and Antitumor: Possible Mechanims of Action," Cancer Research, vol. 65, 2002, pp. 4007-4014.

* cited by examiner

*Primary Examiner*—Brian Kwon
(74) *Attorney, Agent, or Firm*—Pillsbury Winthrop Shaw Pittman LLP

(57) ABSTRACT

Methods of treating a host suffering from restenosis are provided. The methods include delivery of a stent coated with a hypoestoxide, hypoestoxide derivative or hypoestoxide agonist compound to a vessel. The methods further include the administration of a chemotherapeutic agent in combination with delivery of a stent coated with a hypoestoxide, hypoestoxide derivative or hypoestoxide agonist compound to a vessel. The chemotherapeutic agent may be coated on the stent or administered systemically.

13 Claims, No Drawings

HYPOESTOXIDES, DERIVATIVES AND AGONISTS THEREOF FOR USE AS STENT-COATING AGENTS

This application claims the benefit of priority under 35 U.S.C. § 119 of provisional U.S. application Ser. No. 60/480,316, filed Jun. 23, 2003, the contents of which are hereby incorporated by reference in their entirety, as if fully set forth.

FIELD OF THE INVENTION

This invention relates to the delivery of diterpene compounds from intravascular stents. In particular, disclosed herein are hypoestoxides, derivatives and agonists thereof, delivered directly from micropores in a stent body or mixed or bound to a polymer coating applied to the stent, for the purpose of inhibiting neointimal tissue proliferation and thereby prevent restenosis.

CROSS REFERENCE TO RELATED APPLICATIONS

Expressly incorporated herein by reference are: U.S. Pat. Nos. 5,801,193, 5,994,328 and 6,242,484, and co-pending applications, U.S. Ser. Nos. 09/006,946; 09/007,308; 09/298,653; and PCT WO 98/46222.

BACKGROUND OF THE INVENTION

Coronary artery disease (CAD) is a disease that affects the blood vessels that nourish the heart muscle. CAD is a result of atherosclerosis, a build-up of fatty substances on the inner walls of the coronary arteries. When the coronary arteries become clogged or narrowed by these waxy "fats", blood flow is restricted and the heart muscle does not receive adequate oxygen, which can lead to heart attack and even death. In many cases, angina pectoris (chest pain) may occur when the heart is not receiving enough oxygen. The risk of CAD increases with elevated levels of total cholesterol and low-density lipoprotein (LDL) in the blood, but decreases when high-density lipoprotein (HDL) increases. In the United States, cardiovascular diseases are the leading cause of death in both genders, accounting for about one-third of deaths each year; the American Heart Association estimates that more than 12 million people have some form of CAD history. (American Heart Association, *Fighting Heart Disease and Stroke*, 2000, Heart and Stroke Statistical Update, p.5)

The problem of atherosclerosis may extend beyond the heart. Patients with CAD may also have atherosclerosis of the arterial beds including peripheral artery occlusive disease (PAOD), renal artery stenosis (RAS) and cerebrovascular disease (CBVD). This comorbidity results in an increased risk for stroke, myorcardial infarction (MI), cardiovascular death, and renal failure.

Vessels that are narrowed due to atherosclerosis are said to have undergone stenosis. The term "restenosis" refers to a re-narrowing of a vessel after a procedure has been performed to reduce a previous narrowing.

Percutaneous transluminal coronary angioplasty (PTCA) is the procedure generally used to open an obstructed artery. The placement of a balloon expanded stent or a self-expandable stent during PTCA is the leading minimally invasive treatment option. Stents are used in the treatment of new lesions or blockages, and in areas where restenosis has occurred.

A major limitation of PTCA is the problem of post-PTCA closure of the vessel, both immediately after PTCA (acute occlusion) and in the long term (restenosis). Restenosis after angioplasty is a more gradual process and involves initial formation of a subcritical thrombosis with release from adherent platelets of cell derived growth factors, along with subsequent proliferation of intimal smooth muscle cells and local infiltration of inflammatory cells contributing to vascular hyperplasia. It is important to note that multiple processes, including thrombosis, cell proliferation, cell migration and inflammation each seem to contribute to the restenotic process, and that many of these same processes contribute to the initial process of stenosis. Thus, anti-inflammatory and antiproliferative drugs, coated on stents, appear to be the most promising approach to treat various aspects of stenosis and restenosis (Hong, MK, et al., *Paclitaxel-coated Gianturco-Roubin® II (GRII) stents reduce neointimal hyperplasia in a porcine coronary in-stent restenosis model*, Coronary Artery Disease, 2001, Vol. 12, No. 6, pp. 513-515).

Numerous agents have been examined for presumed antiproliferative actions in restenosis and have shown some activity in experimental animal models. Some of the agents which have been shown to successfully reduce the extent of intimal hyperplasia in animal models include: heparin and heparin fragments (Clowes, A. and Kamovsky, M, Nature, 1977, Vol. 265, pp. 25-26), colchicine (Currier, J., et al., Circulation, 1989, Vol. 80, pp. 11-66), taxol (Sollott, S., et al., J. Clin. Invest., 1995, Vol. 95, pp. 1869-1876), cyclosporin A (Jonasson, L, et al., Proc. Natl. Acad. Sci., 1988, Vol. 85, p. 2303) and rapamycin (Marx, S., et al., Circ. Res., 1995, Vol. 76, pp. 412-417). Post-angioplasty restenosis is a multifactorial process that involves numerous interactive mechanisms. This means that effective prevention of restenosis may not be feasible with agents possessing a single mechanism of action. Accordingly, there is a need for multi-faceted approaches to the treatment and prevention of restenosis following PTCA

SUMMARY OF THE INVENTION

Because hypoestoxides have been shown to possess both anti-inflammatory and antiproliferative activities respectively (Ojo-Amaize, E., et al., Cellular Immunology, 2001, Vol. 209, No. 2, pp. 149-157; Ojo-Amaize, E., et al., Cancer Research, 2002, Vol. 62, pp. 4007-4014), it is envisaged that hypoestoxide-eluting stents would be quite effective in treatment and prevention of stenosis and restenosis. The present invention provides methods of treating a host, such as a human, suffering from vascular stenosis, with stents combined with hypoestoxides, derivatives and agonists thereof, such that the vascular stenosis is ameliorated thereby and in such a way as to be effective for prevention of restenosis. The stent-drug combination may result in a better therapeutic effect than would occur with either component alone. The drug may be administered systemically in a therapeutic dose or, alternatively, could be bound to the surface of a stent by means of incorporation within a biodegradable or biostable polymeric coating. Thus, the methods include delivery of a stent to a coronary artery that may be susceptible to stenosis or restenosis, incorporating and delivering from the surface of said stent an effective amount of a compound of formula I:

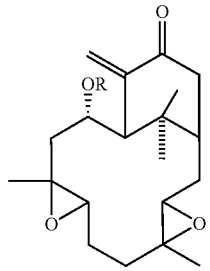
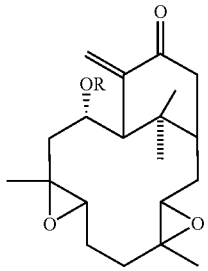

wherein R is:
a) H or acetyl,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds, said alkyl selected from the group consisting of substituted, unsubstituted, straight chain and branched alkyls,
f) (CH$_2$)n morpholine, wherein n=1-4,
g) morpholinomethylphenyl, ortho-aminophenyl or ortho-hydroxyphenyl,
h) (CH$_2$)n COOR$_2$ wherein n=1-4, R$_2$ is each selected from the group consisting of H, an alkali metal salt, an alkaline earth metal salt, NH$_4$+ and N+(R$_3$)$_4$ wherein R$_3$ is each independently selected from the group consisting of H and an alkyl of 1 to 4 carbon atoms, or
i) COR$_1$ wherein R$_1$ is selected from the group consisting of H, (CH$_2$)n CH$_3$ wherein n=0-6, (CH$_2$)n COOR$_2$ wherein n=1-4 and R$_2$ is each selected from the group consisting of H, an alkali metal salt, an alkaline earth metal salt, NH$_4$+ and N+(R$_3$)$_4$, and (CH$_2$)n N+(R$_3$)$_4$ wherein n=1-4 and R$_3$ is each independently selected from the group consisting of H and an alkyl of 1 to 4 carbon atoms, wherein the effective amount is an amount sufficient to ameliorate at least one aspect of restenosis, and wherein the compound may be used alone or in combination with chemotherapeutic agents.

DETAILED DESCRIPTION OF THE INVENTION

As used herein, the term "host" or "subject" is taken to mean human, as well as other animals. The term "ameliorate" means to improve, lessen the severity of or mitigate.

Methods of treating a host suffering from restenosis are provided. In one method, an effective amount of a hypoestoxide, hypoestoxide derivative, or an agonist thereof is coated on a stent with appropriate release kinetics in an amount sufficient to ameliorate at least one aspect of restenosis, as defined above. The method comprises delivery of a stent coated with the hypoestoxide, hypoestoxide derivative, or an agonist thereof to a vessel such as a coronary artery that may be susceptible to stenosis or restenosis. Delivery of the stent is accomplished by PTCA according to methods well known in the art. Accordingly, the stent is coated with an effective amount of a compound of formula I:

wherein R is:
a) H or acetyl,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds, said alkyl selected from the group consisting of substituted, unsubstituted, straight chain and branched alkyls,
f) (CH$_2$)n morpholine, wherein n=1-4,
g) morpholinomethylphenyl, ortho-aminophenyl or ortho-hydroxyphenyl,
h) (CH$_2$)n COOR$_2$ wherein n=1-4, R$_2$ is each selected from the group consisting of H, an alkali metal salt, an alkaline earth metal salt, NH$_4$+ and N+(R$_3$)$_4$ wherein R$_3$ is each independently selected from the group consisting of H and an alkyl of 1 to 4 carbon atoms, or
i) COR$_1$ wherein R$_1$ is selected from the group consisting of H, (CH$_2$)n CH$_3$ wherein n=0-6, (CH$_2$)n COOR$_2$ wherein n=1-4 and R$_2$ is each selected from the group consisting of H, an alkali metal salt, an alkaline earth metal salt, NH$_4$+ and N+(R$_3$)$_4$, and (CH$_2$)n N+(R$_3$)$_4$, wherein n=1-4 and R$_3$ is each independently selected from the group consisting of H and an alkyl of 1 to 4 carbon atoms, wherein the effective amount is an amount sufficient to ameliorate at least one aspect of restenosis.

In another method of treating a host suffering from restenosis, an effective amount of a hypoestoxide, hypoestoxide derivative, or an agonist thereof is coated on a stent with appropriate release kinetics in an amount sufficient to ameliorate at least one aspect of restenosis, as defined above. The method also comprises treatment with one or more standard chemotherapeutic agents, including, but not in any way limited to, rapamycin, taxol, vincristine, paclitaxel, colchicine, dexamethasone and tyrphostin. The method comprises delivery of a stent coated with the hypoestoxide, hypoestoxide derivative, or an agonist thereof to a vessel such as a coronary artery that may be susceptible to stenosis or restenosis. Delivery of the stent is accomplished by PTCA according to methods well known in the art. The chemotherapeutic agents may be co-administered by coating them on the stent or by administering them systemically in a therapeutic dose. Coating of the stent with the chemotherapeutic agents may be accomplished by vapor deposition according to methods well known in the art. A therapeutic dose of a systemically administered chemotherapeutic agent may be in the range of 0.1 micrograms to 1000 milligrams, depending on the chemotherapeutic agent selected. Accordingly, the stent is coated with an effective amount of a compound of formula I:

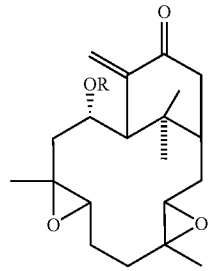

wherein R is:
a) H or acetyl,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds, said alkyl selected from the group consisting of substituted, unsubstituted, straight chain and branched alkyls,
f) (CH$_2$)n morpholine, wherein n=1-4,
g) morpholinomethylphenyl, ortho-aminophenyl or ortho-hydroxyphenyl,
h) (CH$_2$)n COOR$_2$ wherein n=1-4, R$_2$ is each selected from the group consisting of H, an alkali metal salt, an alkaline earth metal salt, NH$_4$+ and N+(R$_3$)$_4$ wherein R$_3$ is each independently selected from the group consisting of H and an alkyl of 1 to 4 carbon atoms, or
i) COR$_1$ wherein R$_1$ is selected from the group consisting of H, (CH$_2$)n CH$_3$ wherein n=0-6, (CH$_2$)n COOR$_2$ wherein n=1-4 and R$_2$ is each selected from the group consisting of H, an alkali metal salt, an alkaline earth metal salt, NH$_4$+ and N+(R$_3$)$_4$, and (CH$_2$)n N+(R$_3$)$_4$, wherein n=1-4 and R$_3$ is each independently selected from the group consisting of H and an alkyl of 1 to 4 carbon atoms, wherein the effective amount is an amount sufficient to ameliorate at least one aspect of restenosis.

Preferred compounds of the invention are compounds of formula I, wherein R=H and R=acetyl (hypoestoxide).

Useful dosages of the compounds of formula I can be determined by comparing their in vivo activity in animal models. Methods for the extrapolation of effective dosages in porcine, and other animals, to humans are known in the art; for example, see U.S. Pat. No. 4,938,949.

Stents coated with hypoestoxide compounds according to the present invention are prepared as follows. Any balloon expandable stent known in the art may be used in accordance with the present invention, including, but not in any way limited to, plastic or stainless steel stents (examples of particular brand names include, but are not in any way limited to, CYPHER™ and Gianturco-Roubin® II). Three of six intravascular stents were coated with a Hypoestoxide (HE) impregnated hydrogel formulation whose HE release kinetics were previously determined to be appropriate over at least a fourteen day period. See Table 1, below, for % cross-linking, composition, and HE release kinetics results.

TABLE 1

HE release kinetics for HE/hydrogel formulations

| *Sample ID | % Crosslinker | Composition | HPLC Results for HE (ng/ml) |
|---|---|---|---|
| 080703C | 12.4 | 0.46869 g HEMA | 1 day . . . saturated |
| | | 0.0212 g PABA | 3 day . . . saturated |
| | | 0.0033 g CQ | 7 day . . . saturated |
| | | 0.00015 g HE | 14 day . . . 7,970 |
| | | 0.0702 g TDGMA | |

The formulation that was chosen was based on the hydrogel that gave the maximum release of HE over time but was also robust enough to withstand the repeated expansion and contraction of the stent. Other formulations are possible, including those with 0%-50% cross-linking. The formulation comprises 2-hydroxyethyl methacrylate (HEMA) which was purified prior to use by fractional distillation and stored at 4° C. The triethylene dimethacrylate (TGDMA) was purified by fractional distillation prior to use and stored at 4° C. The 4-(dimethylamino)-2-ethylhexyl Benzoic acid (aka 2-ethylhexyl dimethyl PABA) abbreviated PABA and the camphorquinone (CQ) were used as commercially available. A blue light (non UV dental type) source was used to initiate the polymerization (Omega #750 light curing unit).

All work was conducted under a class 100-laminar hood. Formulation 080703C was applied to each stent by dipping. The excess was removed to prevent webbing. Stents should be removed from their balloons before application of the HE formulation. The HE formulation was then photopolymerized onto the sample with a blue light for several minutes to insure complete monomer conversion. A target amount of 150 micrograms (0.00015 g) of HE was applied to each stent, although applications of 0.1 micrograms to 1000 micrograms are possible in accordance with the present invention. The coated stents were then redeployed onto the balloons and inspected. After redeployment, the stents were double-bag packaged and sterilized with 100% ethylene oxide. Following sterilization the samples were placed in a vacuum oven at 25° C. overnight to remove any ethylene oxide residuals.

The range of HE/hydrogel formulations described herein offer but one example of formulations that are amenable to incorporation of hypoestoxides, hypoestoxide derivatives and hypoestoxide agonists according to the present invention for deployment on a stent. One skilled in the art will realize that hypoestoxides, hypoestoxide derivatives and hypoestoxide agonists according to the present invention can be incorporated into any suitable polymer for deployment on a stent.

The inhibitory effect of hypoestoxides according to the present invention on platelet aggregation was studied. Platelet-rich plasma from a New Zealand rabbit was used as the source of platelets. Arachidonic acid (100 μM) was used to induce maximal platelet aggregation in vitro. Optical density of aggregation was measured by densitometry. The percent inhibition of the arachidonic acid-induced response is shown in Table 2, below. PAF (Platelet Aggregating Factor), which served as a positive control, induced a 96.5% inhibition while Hypoestoxide induced a complete (100%) inhibition.

Table 2 shows the complete inhibitory effect of hypoestoxides on platelet aggregation. It should be recalled that restenosis, after angioplasty, is a more gradual process which involves initial formation of a subcritical thrombosis with release from adherent platelets of cell derived growth factors responsible for proliferation of intimal smooth muscle cells and local infiltration of inflammatory cells which contribute to vascular hyperplasia. Thus, hypoestoxide-eluting stents with appropriate release kinetics should prevent the initial formation of a subcritical thrombosis over time.

TABLE 2

Hypoestoxides inhibit arachidonic acid-induced platelet aggregation

| Agent | % Inhibition |
| --- | --- |
| Vehicle Control (0.3% DMSO) | 0 |
| Positive Control (0.3 µM PAF) | 96.5 |
| Hypoestoxide (30 µM) | 100 |

The inhibitory effect of hypoestoxides according to the present invention on stenosis was studied in an animal model. It is well known in the art that stent deployment into vessels can be the catalyst for a stenotic response. Thus, the effect of coating stents with hypoestoxides according to the present invention prior to stent deployment was studied. It was found that the hypoestoxide-coated stents inhibited the expected stenotic response, as compared to the presence of the expected stenosis in control stents (i.e., those not coated with hypoestoxide).

Six specific-pathogen-free domestic pigs (approx. 40 kg) were used for the study. Percutaneous transluminal stent deployment into the circumflex artery was performed in the subject animals. Three stents were uncoated (control pigs #983, #987 and #988) and three stents were coated with a hypoestoxide compound according to the present invention (test pigs #982, #989 and #990). The pigs were pretreated orally with 325 mg aspirin and 75 mg plavix three days prior to implantation. The pigs were maintained on the same dosages of plavix and aspirin daily thereafter and were observed for 30 or 45 days post-procedure, at which point they were euthanized and their coronary arteries were harvested.

Angiography was performed quantitatively with use of QCA-CMS version 4.0 (Medical Imaging System, Leiden, The Netherlands) on each animal on the final day before euthanasia. Just prior to euthanasia, each pig was given 2,000 units IV of heparin followed by 5 cc euthasol. After euthanasia, the heart from each pig was excised and the circumflex arteries harvested, examined, and placed in formalin for subsequent microscopic examination.

Table 3, below, shows complete inhibition of stenosis (0% stenosis) in two of the three pigs implanted with hypoestoxide-coated stents (test pigs # 982, and 990 respectively) and 90% inhibition of stenosis (10% stenosis) in test pig # 989 as compared to control pigs implanted with uncoated stents (control pigs # 983 and 988) which showed 30% and 80% stenosis respectively. Pig # 983 was observed for 30 days while pig # 988 was observed for 45 days.

In control pig # 987, the stent had migrated and could not be found. All of the vessels of the heart appeared to be normal. Its heart also appeared to be normal.

During angiography, it was observed that the circumflex artery of control pig # 983 had approximately 30% stenosis at the distal end of the stent. The remaining arteries appeared normal. The circumflex artery of control pig # 983 was bisected at the location of the stent. It was examined with high and low magnification. The stent was well embedded in the wall of the artery, healing well underway, with obvious neointimal formation with restenosis at the distal end of the stent (Pathophysiology of coronary artery restenosis. Robert Schwartz, et. al. Reviews in Cardiovascular Medicine, 3-5, pp. S4-S9, 2002.).

During angiography, it was observed that in the control pig # 988, the circumflex artery had approximately 80% stenosis at the proximal end of the stent. Thrombus was also observed in the proximal end of the stent. While examining the heart of the pig, it was observed that the heart had endotrophic myopathy, it had an infarction, it was hyperkinetic, and had a very hard left ventricle. Its circumflex artery was bisected at the location of the stent. It was examined with high and low magnification. The stent was well embedded in the wall of the artery, healing was well underway, with obvious neointimal formation with stenosis at the distal end of the stent.

In test pigs # 982 and 990, there were no observable stenosis whatsoever (0% stenosis) by angiography. The ventricles and vessels all appeared normal. The circumflex arteries were bisected at the location of the stents. They were examined with high and low magnification. The stents were not embedded in the walls of the arteries. Healing was well underway. The stents were 100% free from obstructions and were easily slid out of the arteries.

In test pig # 989, 10% stenosis at the distal end of the stent was observed by angiography. The ventricles and vessels all appeared normal. The circumflex artery was bisected at the location of the stent. It was examined with high and low magnification. The stent was well embedded in the wall of the artery, healing was well underway, with obvious neointimal formation.

TABLE 3

Hypoestoxide-Coated Stents Prevent Stenosis in Pigs

| Agent | Pig # | % Stenosis | # Days Observed |
| --- | --- | --- | --- |
| Uncoated Stents | 983 | 30 | 30 |
| | 987 | Stent migrated | 45 |
| | 988 | 80 | 45 |
| Hypoestoxide-Coated Stents | 982 | 0 | 30 |
| | 989 | 10 | 45 |
| | 990 | 0 | 45 |

All publications, patents, and patent documents are incorporated by reference herein, as though individually incorporated by reference.

While the description above refers to particular embodiments of the present invention, it should be readily apparent to people of ordinary skill in the art that a number of modifications may be made without departing from the spirit thereof. The accompanying claims are intended to cover such modifications as would fall within the true spirit and scope of the invention. The presently disclosed embodiments are, therefore, to be considered in all respects as illustrative and not restrictive, the scope of the invention being indicated by the appended claims rather than the foregoing description. All changes that come within the meaning of and range of equivalency of the claims are intended to be embraced therein.

What is claimed is:

1. A method of reduction or treatment of restenosis comprising:

delivering an intravascular stent to a vascular lumen of a host in need thereof, wherein said stent is coated with an effective amount in the range of from 0.1 micrograms to 1000 micrograms of a compound having the formula:

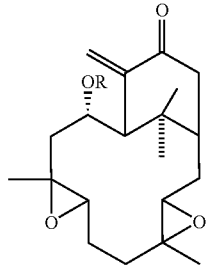

wherein R is selected from the group consisting of:
a) H or acetyl,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds, said alkyl selected from the group consisting of substituted, unsubstituted, straight chain and branched alkyls,
f) (CH$_2$)n morpholine, wherein n=1-4,
g) morpholinomethylphenyl, ortho-aminophenyl or ortho-hydroxyphenyl,
h) (CH$_2$)n COOR$_2$ wherein n=1-4, R$_2$ is each selected from the group consisting of H, an alkali metal salt, an alkaline earth metal salt, NH$_4$ + and N+(R$_3$)$_4$ wherein R$_3$ is each independently selected from the group consisting of H and an alkyl of 1 to 4 carbon atoms, and
i) COR$_1$ wherein R$_1$ is selected from the group consisting of H, (CH$_2$)n CH$_3$ wherein n=0-6, and (CH$_2$)n COOR$_2$ wherein n=1-4 and R$_2$ is each selected from the group consisting of H, an alkali metal salt, an alkaline earth metal salt, NH$_4$ +, N+(R$_3$)$_4$ and (CH$_2$)n N+(R$_3$)$_4$, wherein n=1-4 and R$_3$ is each independently selected from the group consisting of H and an alkyl of 1 to 4 carbon atoms, wherein the effective amount is to reduce or treat restenosis.

2. The method of claim 1, wherein R is selected from the group consisting of H and acetyl.

3. The method of claim 1, wherein R is acetyl.

4. The method of claim 1, wherein the stent is coated with an amount of the compound in the range from 100-200 micrograms.

5. The method of claim 1, wherein the compound is incorporated in a hydrogel formulation.

6. A method of and/or treatment of restenosis comprising:
delivering an intravascular stent to a vascular lumen of a host in need thereof, wherein said stent is coated with an effective amount in the range of from 0.1 micrograms to 1000 micrograms of a compound having the formula:

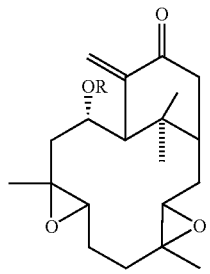

wherein R is selected from the group consisting of:
a) H or acetyl,
b) P(O)(OH)$_2$,
c) P(O)(OH)(OM), wherein M is selected from the group consisting of an alkali metal salt and an alkaline earth metal salt,
d) P(O)OM$_2$ wherein M is each independently selected from the group consisting of alkali metal salts and alkaline earth metal salts,
e) Alkyl of 1 to 12 carbon atoms having 0 to 6 double bonds, said alkyl selected from the group consisting of substituted, unsubstituted, straight chain and branched alkyls,
f) (CH$_2$)n morpholine, wherein n=1-4,
g) morpholinomethylphenyl, ortho-aminophenyl or ortho-hydroxyphenyl,
h) (CH$_2$)n COOR$_2$ wherein n=1-4, R$_2$ is each selected from the group consisting of H, an alkali metal salt, an alkaline earth metal salt, NH$_4$ + and N+(R$_3$)$_4$ wherein R$_3$ is each independently selected from the group consisting of H and an alkyl of 1 to 4 carbon atoms, and
i) COR$_1$ wherein R$_1$ is selected from the group consisting of H, (CH$_2$)n CH$_3$ wherein n=0-6, and (CH$_2$)n COOR$_2$ wherein n=1-4 and R$_2$ is each selected from the group consisting of H, an alkali metal salt, an alkaline earth metal salt, NH$_4$ +, N+(R$_3$)$_4$ and (CH$_2$)n N+(R$_3$)$_4$, wherein n=1-4 and R$_3$ is each independently selected from the group consisting of H and an alkyl of 1 to 4 carbon atoms, and;
the administration of at least one chemotherapeutic agent, wherein at least one chemotherapeutic agent is selected from the group consisting of rapamycin, taxol, vincristine, colchicine, dexamethasone and tyrphostin, wherein the effective amount is to treat restenosis.

7. The method of claim 6, wherein R is selected from the group consisting of H and acetyl.

8. The method of claim 6, wherein R is acetyl.

9. The method of claim 6, wherein the stent is coated with an amount of the compound in the range from 100-200 micrograms.

10. The method of claim 9, wherein the compound is incorporated in a hydrogel formulation.

11. The method of claim 6, wherein at least one of the chemotherapeutic agent is coated on the stent.

12. The method of claim 11, wherein the coating is accomplished by vapor deposition.

13. The method of claim 6, wherein at least one of the chemotherapeutic agent is administered systemically.

* * * * *